(12) United States Patent
Huddart et al.

(10) Patent No.: US 10,357,625 B2
(45) Date of Patent: Jul. 23, 2019

(54) BREATHABLE RESPIRATORY MASK

(71) Applicant: Fisher & Paykel Healthcare Limited, Auckland (NZ)

(72) Inventors: Brett John Huddart, Auckland (NZ); Denny Adianto Purnomo, Auckland (NZ); Kevin Blake Powell, Auckland (NZ); Bhavna Patel, Auckland (NZ); Emma Louise Duckworth, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 520 days.

(21) Appl. No.: 14/661,314

(22) Filed: Mar. 18, 2015

(65) Prior Publication Data
US 2016/0008563 A1   Jan. 14, 2016

Related U.S. Application Data

(63) Continuation of application No. 10/921,572, filed on Aug. 19, 2004, now Pat. No. 8,997,743.

(30) Foreign Application Priority Data

Sep. 17, 2003   (NZ) .......................... 528326

(51) Int. Cl.
*A61M 16/00*   (2006.01)
*A61M 16/06*   (2006.01)
*A61M 16/10*   (2006.01)

(52) U.S. Cl.
CPC ........ *A61M 16/06* (2013.01); *A61M 16/0605* (2014.02); *A61M 16/0683* (2013.01);
(Continued)

(58) Field of Classification Search
CPC .......... A61M 16/06; A61M 2016/0661; A61M 16/0688; A61M 16/0605; A61M 16/0683;
(Continued)

(56) References Cited

U.S. PATENT DOCUMENTS

| 893,213 A | 7/1908 | Whiteway |
|---|---|---|
| 1,079,227 A | 11/1913 | Fanning |

(Continued)

FOREIGN PATENT DOCUMENTS

| CA | 2833707 | 11/2001 |
|---|---|---|
| CA | 2346628 | 7/2010 |

(Continued)

OTHER PUBLICATIONS

Philip Gibson, Effect of Temperature on Water Vapor Transport Through Polymer Membrane Laminates, Technical Report Natick/TR-99/015, pp. 1-41.

(Continued)

*Primary Examiner* — Steven O Douglas
(74) *Attorney, Agent, or Firm* — Knobbe, Martens, Olson & Bear LLP

(57) ABSTRACT

A patient interface which is comfortable for the user to wear can include at least in part a moisture permeable or breathable area in the body of the patient interface. The patient interface can be a strapless mask that is molded to fit the contours of a user's face and maximize the mask-to-skin seal. An adhesive material is bonded to the mask cushion and is stamped in place to form substantially the same shape as the cushion such that it fits the facial contours of the user.

19 Claims, 18 Drawing Sheets

(52) U.S. Cl.
CPC .... *A61M 16/0688* (2014.02); *A61M 16/1045* (2013.01); *A61M 2016/0661* (2013.01); *A61M 2205/02* (2013.01); *A61M 2205/0222* (2013.01)

(58) Field of Classification Search
CPC .......... A61M 16/1045; A61M 2205/02; A61M 2205/0222
USPC ............ 128/206.24, 205.25, 206.27, 206.28, 128/206.21, 207.11, 201.13, 204.17, 128/206.19, 204.15, 204.16, 203.16, 128/203.26, 205.27; 607/114, 96, 607/109–112, 99, 104; 96/4; 55/DIG. 35
See application file for complete search history.

(56) References Cited

U.S. PATENT DOCUMENTS

| | | |
|---|---|---|
| 1,990,199 A | 2/1935 | Nemzek |
| 2,281,181 A | 4/1942 | Clarke |
| 2,791,216 A | 5/1957 | Adrian et al. |
| 2,868,199 A | 1/1959 | Hudson |
| 2,931,356 A | 4/1960 | Schwarz |
| 3,144,313 A | 8/1964 | Pfefferie |
| 3,154,073 A | 10/1964 | Klinger |
| 3,228,877 A | 1/1966 | Mahon |
| 3,245,206 A | 4/1966 | Bonnet |
| 3,292,346 A | 12/1966 | Adams |
| 3,303,105 A | 2/1967 | Konikoff et al. |
| 3,307,330 A | 3/1967 | Niedzielski et al. |
| 3,315,674 A | 4/1967 | Aaron et al. |
| 3,367,850 A | 2/1968 | Johnson |
| 3,434,471 A | 3/1969 | Liston |
| 3,513,844 A | 5/1970 | Smith |
| 3,521,630 A | 7/1970 | Westberg et al. |
| 3,639,970 A | 2/1972 | Larkin |
| 3,664,335 A | 5/1972 | Boucher et al. |
| 3,682,171 A | 8/1972 | Dali et al. |
| 3,735,558 A | 5/1973 | Skarstrom et al. |
| 3,735,559 A | 5/1973 | Salemme |
| 3,754,552 A | 8/1973 | King |
| 3,803,810 A | 4/1974 | Rosenberg |
| 3,856,051 A | 12/1974 | Bain |
| 3,889,717 A | 6/1975 | Obadal et al. |
| 3,891,556 A | 6/1975 | Ricahrdson et al. |
| 3,895,630 A | 7/1975 | Bachman |
| 3,910,808 A | 10/1975 | Steward |
| 3,912,795 A | 10/1975 | Jackson |
| 3,963,856 A | 6/1976 | Carlson et al. |
| 3,966,525 A | 6/1976 | Steward |
| 4,007,737 A | 2/1977 | Paluch |
| 4,048,993 A | 9/1977 | Dobritz |
| 4,104,016 A | 8/1978 | Baysinger |
| 4,194,041 A | 3/1980 | Gore et al. |
| 4,204,562 A | 5/1980 | Kelly |
| 4,207,457 A | 6/1980 | Haglunc et al. |
| 4,216,769 A | 8/1980 | Grimes |
| 4,262,704 A | 4/1981 | Grawey |
| 4,265,235 A | 5/1981 | Fukunaga |
| 4,265,239 A | 5/1981 | Fischer, Jr. et al. |
| 4,327,718 A | 5/1982 | Cronenberg |
| 4,327,775 A | 5/1982 | Tally |
| 4,336,798 A | 6/1982 | Beran |
| 4,337,800 A | 7/1982 | Carlson et al. |
| 4,343,672 A | 8/1982 | Kanao |
| 4,344,999 A | 8/1982 | Gohlke |
| 4,406,283 A | 9/1983 | Bir |
| 4,409,283 A | 10/1983 | Bir |
| 4,420,016 A | 12/1983 | Nichols |
| 4,456,034 A | 6/1984 | Bixby |
| 4,462,397 A | 7/1984 | Suzuki |
| 4,463,755 A | 8/1984 | Suzuki |
| 4,469,495 A | 9/1984 | Hiraizumi et al. |
| 4,490,575 A | 12/1984 | Kutnyak |
| 4,509,359 A | 4/1985 | Gedeon et al. |
| 4,601,287 A | 7/1986 | Royce, Jr. |
| 4,653,542 A | 3/1987 | Tascher |
| 4,682,010 A | 7/1987 | Drapeau et al. |
| 4,686,354 A | 8/1987 | Makin |
| 4,698,890 A | 10/1987 | Neaves |
| 4,705,543 A | 11/1987 | Kertzman |
| 4,708,831 A | 11/1987 | Elsworth et al. |
| 4,722,334 A | 2/1988 | Blackmer et al. |
| 4,753,233 A | 6/1988 | Grimes |
| 4,771,770 A | 9/1988 | Artemenko et al. |
| 4,773,410 A | 9/1988 | Blackmer et al. |
| 4,791,963 A | 12/1988 | Gronert et al. |
| 4,808,201 A | 2/1989 | Kertzman |
| 4,825,863 A | 5/1989 | Dittmar et al. |
| 4,844,719 A | 7/1989 | Toyomoto et al. |
| 4,846,170 A | 7/1989 | McAnalley et al. |
| 4,875,908 A | 10/1989 | Kikukawa et al. |
| 4,915,104 A | 4/1990 | Marcy |
| 4,915,105 A | 4/1990 | Lee |
| 4,967,744 A | 11/1990 | Chua |
| 4,995,384 A | 2/1991 | Keeling |
| 5,042,500 A | 8/1991 | Norlien et al. |
| 5,044,361 A | 9/1991 | Werner et al. |
| 5,046,531 A | 9/1991 | Kanao |
| 5,160,511 A | 11/1992 | Lovelock |
| 5,165,395 A | 11/1992 | Ricci |
| 5,230,119 A | 7/1993 | Woods et al. |
| 5,233,996 A | 8/1993 | Coleman et al. |
| 5,273,032 A | 12/1993 | Borody |
| 5,284,160 A | 2/1994 | Dryden |
| 5,335,656 A | 8/1994 | Bowe et al. |
| 5,357,948 A | 10/1994 | Eilentropp |
| 5,392,770 A | 2/1995 | Clawson et al. |
| 5,411,474 A | 5/1995 | Ott et al. |
| 5,427,291 A | 6/1995 | Smith |
| 5,454,061 A | 9/1995 | Carlson |
| 5,461,122 A | 10/1995 | Yilgor et al. |
| 5,462,048 A | 10/1995 | Lambert et al. |
| 5,501,212 A | 3/1996 | Psaros |
| 5,513,634 A | 5/1996 | Jackson |
| 5,521,273 A | 5/1996 | Yilgor et al. |
| 5,586,551 A | 12/1996 | Hillard |
| 5,595,173 A | 1/1997 | Dodd, Jr. |
| 5,595,174 A | 1/1997 | Gwaltney |
| 5,603,317 A | 2/1997 | Farmer |
| 5,603,991 A | 2/1997 | Kupiecki et al. |
| 5,611,332 A | 3/1997 | Bono |
| 5,614,588 A | 3/1997 | Steenblock et al. |
| 5,620,500 A | 4/1997 | Fukui et al. |
| 5,630,409 A | 5/1997 | Bono et al. |
| 5,637,168 A | 6/1997 | Carlson |
| 5,640,951 A | 6/1997 | Huddart et al. |
| 5,653,228 A | 8/1997 | Byrd |
| 5,704,344 A | 1/1998 | Cole |
| 5,709,762 A | 1/1998 | Rowan |
| 5,715,814 A | 2/1998 | Ebers |
| 5,769,071 A | 6/1998 | Turnbull |
| 5,798,013 A | 8/1998 | Brandenburger |
| 5,848,223 A | 12/1998 | Carlson |
| 5,863,312 A | 1/1999 | Wolfe |
| 5,894,839 A | 4/1999 | Rosenkoetter et al. |
| 5,964,219 A | 10/1999 | Pekka |
| 5,975,144 A | 11/1999 | Akedo et al. |
| 5,983,896 A | 11/1999 | Fukunaga et al. |
| 6,078,730 A | 6/2000 | Huddart et al. |
| 6,098,615 A | 8/2000 | Lloyd et al. |
| 6,105,576 A | 8/2000 | Clawson et al. |
| 6,116,235 A | 9/2000 | Walters et al. |
| 6,119,694 A | 9/2000 | Correa |
| 6,148,818 A | 11/2000 | Pagan |
| 6,167,883 B1 | 1/2001 | Beran et al. |
| 6,176,239 B1 | 1/2001 | Grove et al. |
| 6,192,941 B1 | 2/2001 | Mallen-Herrero et al. |
| 6,196,223 B1 | 3/2001 | Belfer et al. |
| 6,201,223 B1 | 3/2001 | Nitta |
| 6,272,933 B1 | 8/2001 | Gradon et al. |
| 6,341,606 B1 | 1/2002 | Bordeweick et al. |
| 6,349,722 B1 | 2/2002 | Gradon et al. |
| 6,357,440 B1 | 3/2002 | Hansen et al. |

(56) References Cited

U.S. PATENT DOCUMENTS

| | | |
|---|---|---|
| 6,363,930 B1 | 3/2002 | Clawson et al. |
| 6,367,472 B1 | 4/2002 | Koch |
| 6,367,510 B1 | 4/2002 | Carlson |
| 6,375,724 B1 | 4/2002 | Foti |
| 6,394,145 B1 | 5/2002 | Bailly |
| 6,412,481 B1 | 7/2002 | Bienvenu et al. |
| 6,432,169 B1 | 8/2002 | Kluwe et al. |
| 6,474,335 B1 | 11/2002 | Lammers |
| 6,516,798 B1 | 2/2003 | Davies |
| 6,523,538 B1 | 2/2003 | Wikefeldt |
| 6,536,136 B2 | 3/2003 | McGlothen |
| 6,536,428 B1 | 3/2003 | Smith et al. |
| 6,536,436 B1 | 3/2003 | McGlothen |
| 6,539,937 B1 | 4/2003 | Havari |
| 6,561,219 B1 | 5/2003 | Apostolides |
| 6,581,594 B1 | 6/2003 | Drew et al. |
| 6,584,972 B2 | 7/2003 | McPhee |
| 6,595,215 B2 | 7/2003 | Wood |
| 6,615,834 B2 | 9/2003 | Gradon et al. |
| 6,637,434 B2 | 10/2003 | Noble |
| 6,662,802 B2 | 12/2003 | Smith et al. |
| 6,701,926 B2 | 3/2004 | Olsen et al. |
| 6,769,431 B2 | 8/2004 | Smith et al. |
| 6,769,432 B1 | 8/2004 | Keifer |
| 6,779,522 B2 | 8/2004 | Smith et al. |
| 6,807,967 B2 | 10/2004 | Wood |
| 6,824,557 B2 | 11/2004 | Tone et al. |
| 6,851,429 B2 | 2/2005 | Bishop |
| 7,036,503 B2 | 5/2006 | Miyazawa et al. |
| 7,140,366 B2 | 11/2006 | Smith et al. |
| 7,493,902 B2 | 2/2009 | White et al. |
| RE40,806 E | 6/2009 | Gradon et al. |
| 7,600,430 B2 | 10/2009 | Palin et al. |
| 7,900,628 B2 | 3/2011 | Matula et al. |
| 7,905,232 B2 | 3/2011 | Olsen et al. |
| 8,037,882 B2 | 10/2011 | Smith et al. |
| 8,220,463 B2 | 7/2012 | White et al. |
| 8,267,092 B2 | 9/2012 | White et al. |
| 8,851,076 B2 | 10/2014 | White et al. |
| 8,905,082 B2 | 12/2014 | Gray |
| 8,980,036 B2 | 3/2015 | Smith et al. |
| 8,997,743 B2 | 4/2015 | Huddart et al. |
| 9,067,035 B2 | 6/2015 | Ophir et al. |
| 9,789,274 B2 | 10/2017 | Madaus et al. |
| 9,802,020 B2 | 10/2017 | Smith et al. |
| 9,827,393 B2 | 11/2017 | Smith et al. |
| 9,849,262 B2 | 12/2017 | White et al. |
| 9,878,120 B2 | 1/2018 | White et al. |
| 2001/0054422 A1 | 12/2001 | Smith et al. |
| 2002/0002976 A1 | 1/2002 | Smith et al. |
| 2002/0014241 A1 | 2/2002 | Gradon et al. |
| 2002/0046755 A1 | 4/2002 | De Voss |
| 2002/0055685 A1 | 5/2002 | Levitsky et al. |
| 2002/0059935 A1 | 5/2002 | Wood |
| 2002/0195104 A1 | 12/2002 | Fini et al. |
| 2003/0028139 A1 | 2/2003 | Inoue |
| 2003/0047185 A1 | 3/2003 | Olsen et al. |
| 2003/0070680 A1 | 4/2003 | Smith et al. |
| 2004/0035428 A1 | 2/2004 | Olsen et al. |
| 2004/0099268 A1 | 5/2004 | Smith et al. |
| 2005/0145250 A1 | 7/2005 | Miyazawa et al. |
| 2007/0235100 A1 | 10/2007 | Tomerlin et al. |
| 2008/0007298 A1 | 3/2008 | Burrowes et al. |
| 2009/0025724 A1 | 1/2009 | Herron, Jr. |
| 2009/0088656 A1 | 4/2009 | Levitsky et al. |
| 2009/0126817 A1 | 5/2009 | Gray |
| 2013/0098360 A1 | 4/2013 | Hurmez et al. |
| 2014/0180157 A1 | 6/2014 | Levitsky et al. |
| 2015/0083125 A1 | 3/2015 | White et al. |
| 2015/0208953 A1 | 7/2015 | Levitsky et al. |
| 2015/0306333 A1 | 10/2015 | Armadio et al. |
| 2016/0045702 A1 | 2/2016 | Milne et al. |
| 2017/0087323 A1 | 3/2017 | White et al. |
| 2017/0087325 A1 | 3/2017 | Wright et al. |
| 2017/0119989 A1 | 3/2017 | White et al. |
| 2017/0296769 A1 | 10/2017 | Smith et al. |
| 2018/0071477 A1 | 3/2018 | Smith et al. |
| 2018/0071478 A1 | 3/2018 | Smith et al. |

FOREIGN PATENT DOCUMENTS

| | | |
|---|---|---|
| CA | 2697142 | 2/2014 |
| DE | 28036 | 2/1984 |
| DE | 4425051 | 5/1995 |
| EP | 0535379 | 4/1993 |
| EP | 0557040 | 8/1993 |
| EP | 0621050 | 10/1994 |
| EP | 1163923 | 12/2001 |
| EP | 1166814 | 1/2002 |
| EP | 1477200 | 10/2006 |
| EP | 1153627 | 11/2007 |
| EP | 1885460 | 2/2008 |
| EP | 1681071 | 2/2009 |
| EP | 2226341 | 9/2010 |
| EP | 2305336 | 4/2011 |
| EP | 2025359 | 9/2013 |
| EP | 2666795 | 11/2013 |
| FR | 2638361 | 5/1990 |
| GB | 587163 | 4/1947 |
| GB | 2176404 | 12/1986 |
| GB | 2228420 | 8/1990 |
| GB | 2252515 | 12/1992 |
| GB | 2139110 | 11/1994 |
| JP | S62-236724 | 10/1987 |
| JP | 03-168155 | 7/1991 |
| JP | H05-052378 | 3/1993 |
| JP | 10248935 | 9/1998 |
| JP | 11323899 | 11/1999 |
| JP | 2000-24111 | 1/2000 |
| JP | 2000-24113 | 1/2000 |
| WO | WO 1997/18001 | 5/1997 |
| WO | WO 00/50121 | 8/2000 |
| WO | WO 00/76568 | 12/2000 |
| WO | WO 2001/041854 | 6/2001 |
| WO | WO 2006/120683 | 11/2006 |
| WO | WO 2012/077052 | 6/2012 |

OTHER PUBLICATIONS

A printout of the frequently asked questions section from www.sympatex.com; Sympatex: How does the Sympatex membrate work? One page.

United States Trademark Registration No. 1,415,873 dates Nov. 4, 1986 for the mark SYMPATEX; Regsitered to Enka America Inc.

Jena et al., Characterization of Water Vapor Permeable Membranes, Desalination 149 (2002) pp. 471-476.

One page off the Perma Pure Inc. website of the product brochure #104 of the New PD TM—Series Gas Dryers (no date).

Three pages off the SympaTex website of some of the most common questions that are asked and some technical data on the SympaTex membrane (no date).

Australian Patent Application No. 200143823 Published on Nov. 15, 2001 entitled Components for Breathing Cirucuits; Inventors Smith, Baldwin, Powell and Millar.

BREATHABLE RESPIRATORY MASK

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to patient interfaces particularly though not solely for use in delivering artificial respiration therapy to patients requiring respiratory humidification treatment. In particular the present invention relates to a mask with a moisture permeable or breathable body and an improved sealing mechanism.

Description of the Related Art

In the art of respiration devices, there are well known variety of respiratory masks which cover the nose and/or mouth of a human user in order to provide a continuous seal around the nasal and/or oral areas of the user's face such that gas may be provided at positive pressure within the mask for consumption by the user. The uses for such masks range from high altitude breathing (i.e., aviation applications) to mining and fire fighting applications, to various medical diagnostic and therapeutic applications.

One application of such a mask is in respiratory humidification treatment. This system normally consists of a ventilator, humidifier, breathing circuit and user interface, being a mask. In this form of treatment humid air is supplied to the patient and as a result of the temperature difference between the humid air and the surrounding environment, the humid air can condense and form water droplets. In cases where treatment is prolonged (up to several days) these droplets may form water pools in the mask that can hamper the treatment, increase the risk of the patient inadvertently inhaling water and may cause discomfort to the patient.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. Nos. 6,196,223 and 6,341,606 are examples of prior art that attempts to improve the mask system. U.S. Pat. No. 5,715,814 is an example of an attempt to improve the mask sealing mechanism.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a device for delivering a supply of gases to a user comprising or including: a patient interface, in use in fluid communication with said supply of gases and adapted to provide a substantially sealed flow path for said flow of gases to said user, said patient interface including a body and a sealing member configured to in use rest against the face of a user, at least one moisture permeable area in said body.

Preferably said moisture permeable area is breathable.

Preferably said patient interface has headgear adapted to attach to or around the head of said user.

Preferably said body has a plurality of sliding members connecting said headgear to said patient interface when said patient interface is engaged with said user.

Preferably said patient interface body has a plurality of cut-out areas producing a framework.

Preferably said at least one moisture permeable area is a plurality of cut-out areas covered with a moisture permeable film, and said body is a framework.

Preferably said moisture permeable film is attached to the inner surface of said framework.

Preferably said patient interface has a plurality of slots cut-out of said patient interface body.

Preferably said slots and said patient interface body is covered by said moisture permeable film.

Preferably a rigid mesh is attached to the inner surface of said framework to form said body.

Preferably said moisture permeable film is attached to the inner surface of said rigid mesh and said framework.

Preferably said patient interface further includes an adhesive member stamped to said sealing member configured to in use rest against the face of the user.

Preferably said sealing member in use remains attached to the user's face for the duration of the treatment.

BRIEF DESCRIPTION OF THE DRAWINGS

Preferred forms of the present invention will now be described with reference to the accompanying drawings.

DETAILED DESCRIPTION OF THE PREFERRED EMBODIMENT

The present invention provides improvements in the delivery of respiratory therapy. In particular a patient interface is described which is comfortable for the user to wear and includes at least in part a moisture permeable and preferably breathable area in the body of the patient interface. It will be appreciated that the patient interface as described in the preferred embodiment of the present invention can be used in respiratory care generally or with a ventilator but will now be described below with reference to use in a humidified Positive Airway Pressure (PAP) system. It will also be appreciated that the present invention can be applied to, nasal masks, oral masks, and combination nasal-oral masks or full-face masks.

Figure 1:
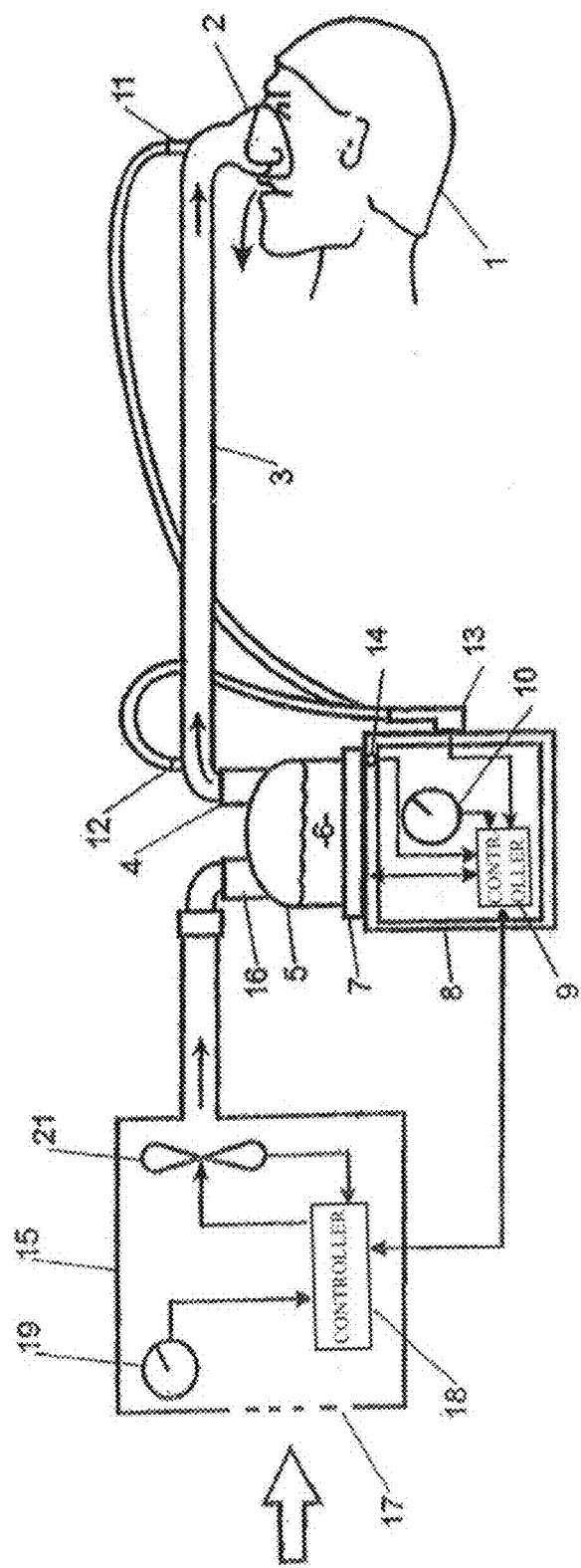
FIG. 1 is a block diagram of a humidified continuous positive airway pressure (CPAP system) as might be used in conjunction with the patient interface of the present invention.

With reference to FIG. 1 a humidified PAP system is shown in which a patient 1 is receiving humidified and pressurised gases through a patient interface 2 connected to a humidified gases transportation pathway or inspiratory conduit 3. It should be understood that delivery systems could also be continuous, variable or bi-level positive airway pressure or numerous other forms of respiratory therapy. The inspiratory conduit 3 is connected to the outlet 4 of a humidification chamber 5 which contains a volume of water 6. The inspiratory conduit 3 may contain heating means or heater wires (not shown) which heat the walls of the conduit to reduce condensation of humidified gases within the conduit. The humidification chamber 5 is preferably formed from a plastics material and may have a highly heat conductive base (for example an aluminium base) which is in direct contact with a heater plate 7 of humidifier 8. The humidifier 8 is provided with control means or electronic controller 9 which may comprise a microprocessor based controller executing computer software commands stored in associated memory.

The controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1 ore returned to the ventilator via a return tube (not shown).

The blower 15 is provided with variable pressure regulating means or variable speed fan 21 which draws air or other gases through blower inlet 17. The speed of variable speed fan 21 is controlled by electronic controller 18 (or alternatively the function of controller 18 could be carried out by controller 9) in response to inputs from controller 9 and a user set predetermined required value (preset value) of pressure or fan speed via dial 19.

Respiratory Mask

Figure 2:
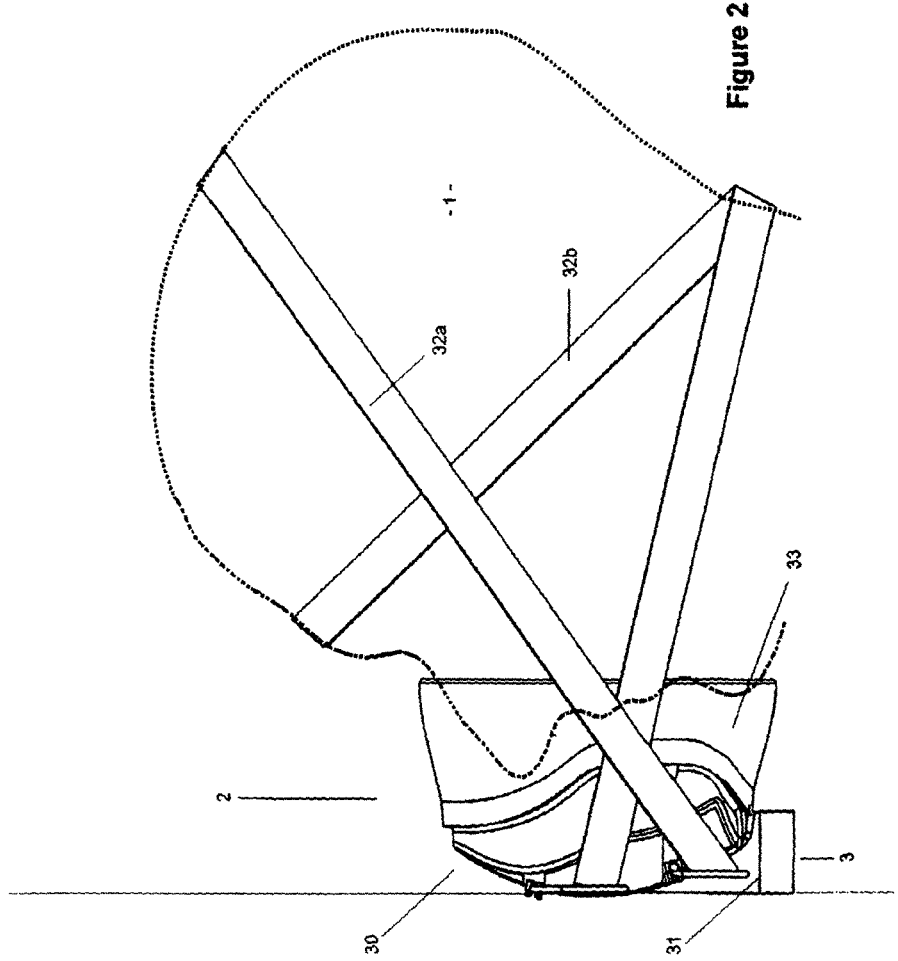
FIG. 2 is an illustration of the patient interface according to a first embodiment of the present invention.
Figure 3:
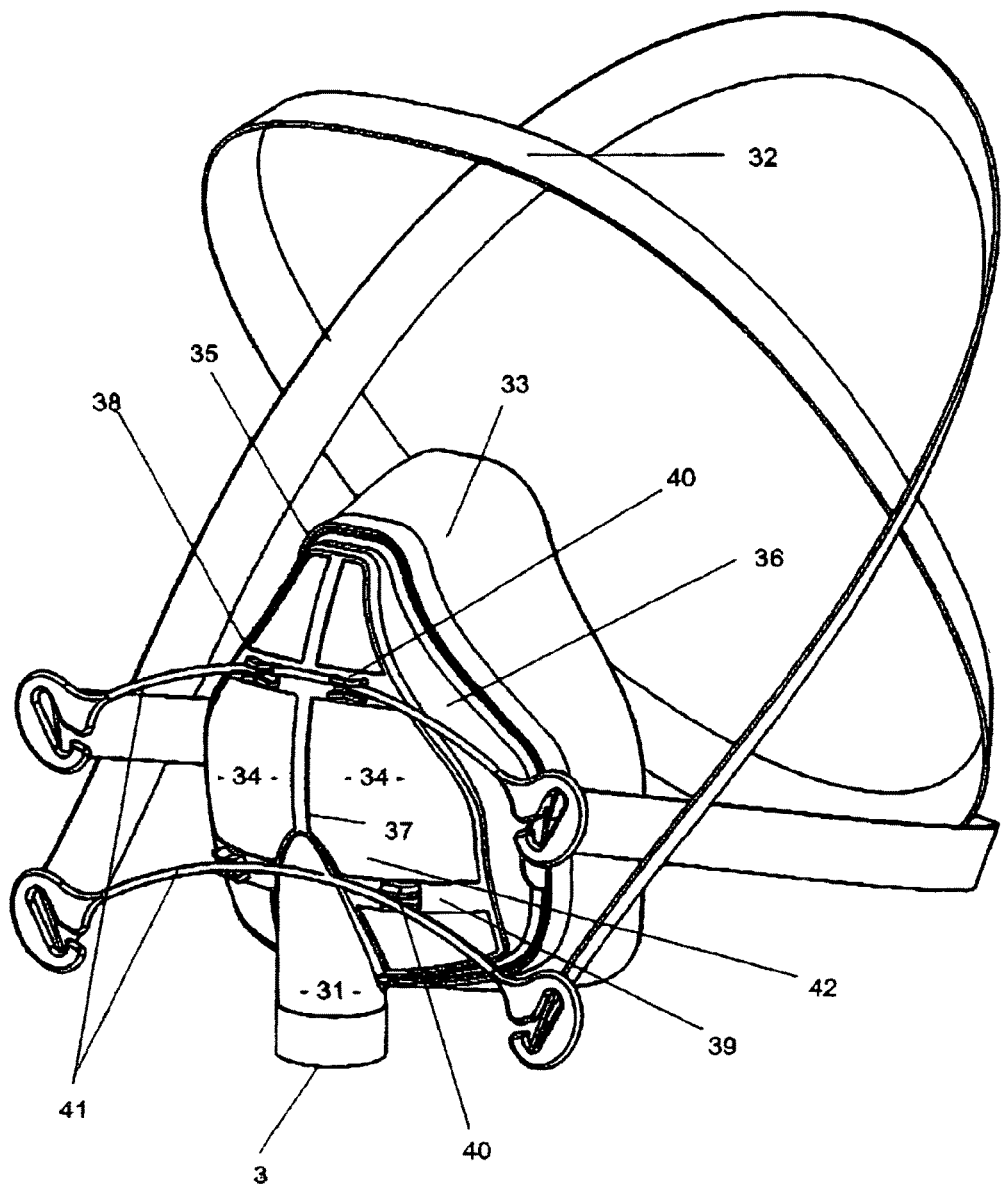
FIG. 3 is a front view of the patient interface body of FIG. 2 showing the upper and lower engaging clips, sliding straps and headgear attachment.
Figure 4:
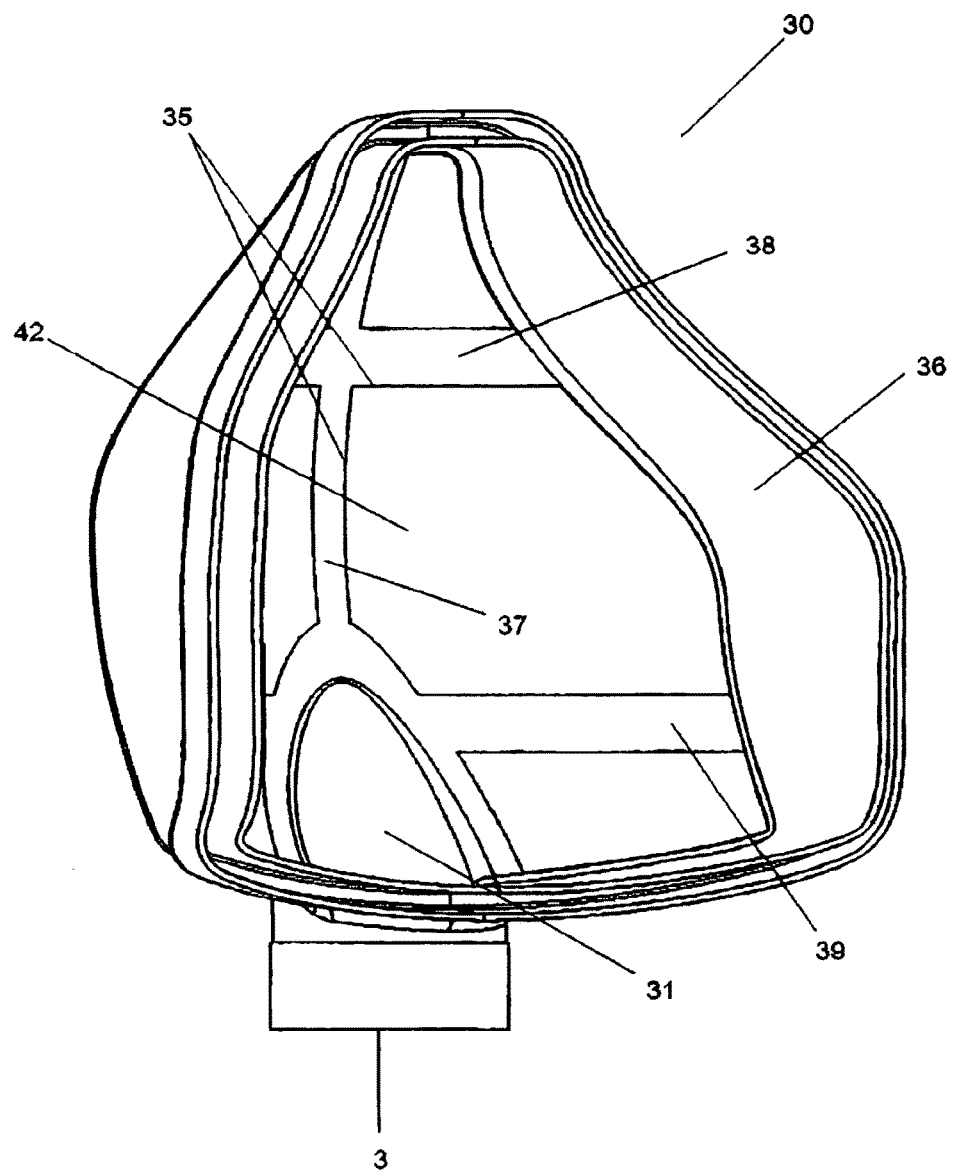
FIG. 4 is a rear view of the patient interface of FIG. 2 illustrating the bead sealing arrangement.

According to a first embodiment of the present invention the patient interface is shown in FIGS. 2, 3 and 4 as a nasal-oral mask. It will be appreciated the patient interface could equally be a nasal mask, oral mask or full-face mask. The mask 2 includes a hollow body 30 with an inlet 31 connected to the inspiratory conduit 3. The mask 2 is positioned on the face of the user 1 with the headgear 32 secured around the back of the head of the patient 1. The restraining force from the headgear 32 on the hollow body 30 ensures enough compressive force on the mask cushion 33, to provide an effective seal against the user's face.

The hollow body 30 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art. The hollow body 30 has areas cut out 34 of the front surface such that the hollow body 30 substantially consists of a framework 35 having an outer circumference surface 36, a vertical member 37 extending from the apex of the outer circumference surface 36 to the apex of the inlet 31, plus an upper horizontal cross-member 38 and a lower horizontal cross-member 39. A number of engaging clips 40 are connected to the upper and lower horizontal members 38 and 39 respectively for the attachment of sliding members 41 to connect the patient interface 2 to the headgear 32. A moisture permeable or breathable film 42 is bonded to the inner surfaces of the hollow body frame 35 to cover the cut-out areas 34 in order to prevent or reduce the formation of water droplets inside the mask 2 during prolonged humidification treatment thereby allowing moisture to escape to the surrounding environment. A number of techniques exist as a means of attaching the moisture permeable film 42 to the hollow body frame 35 which may include gluing, sonic welding techniques, over-moulding or a snaptight connection between the moisture permeable film surface 42 and the hollow body frame 35.

Figure 5:
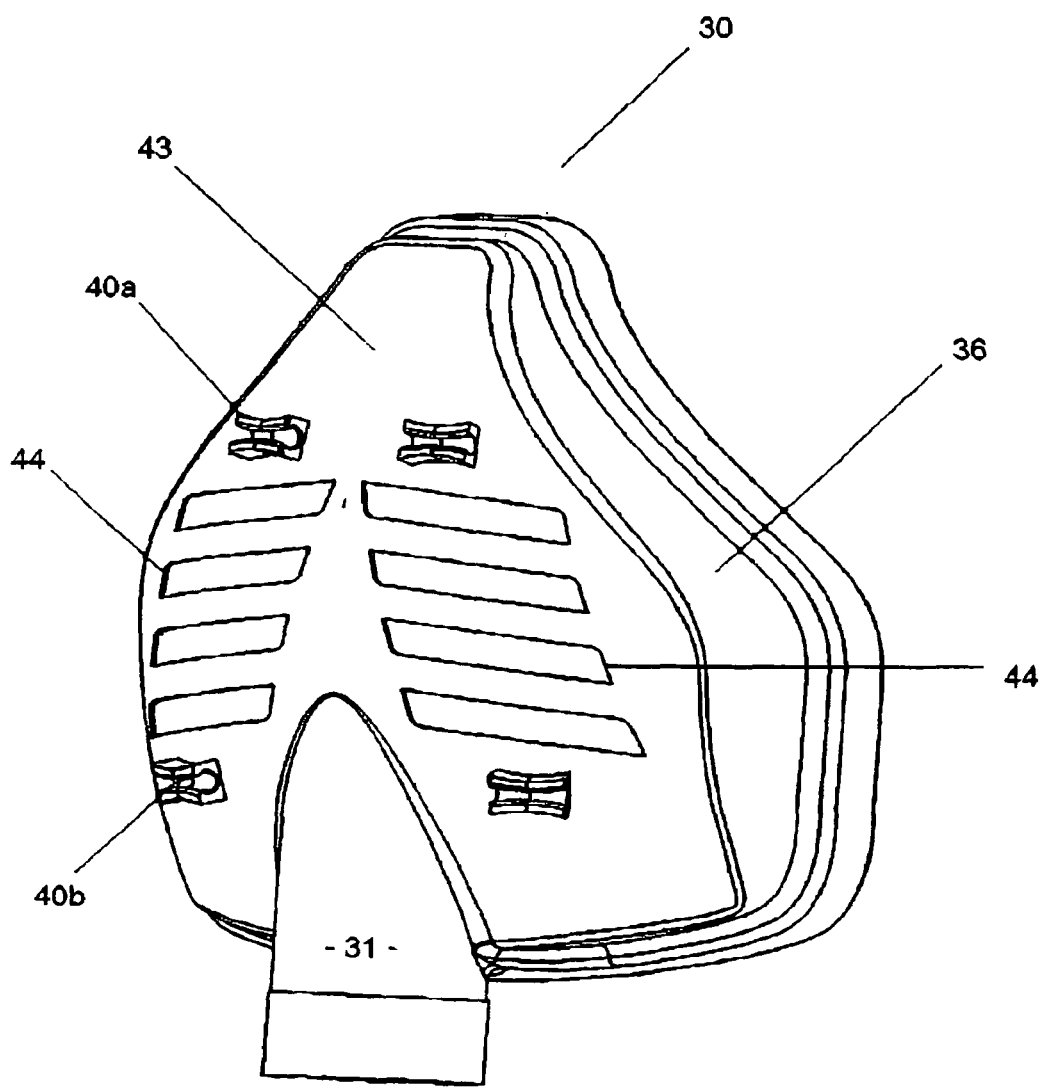
FIG. 5 is a front view of a second embodiment of a patient interface of the present invention were the interface body has chevron cut-out areas.
Figure 6:
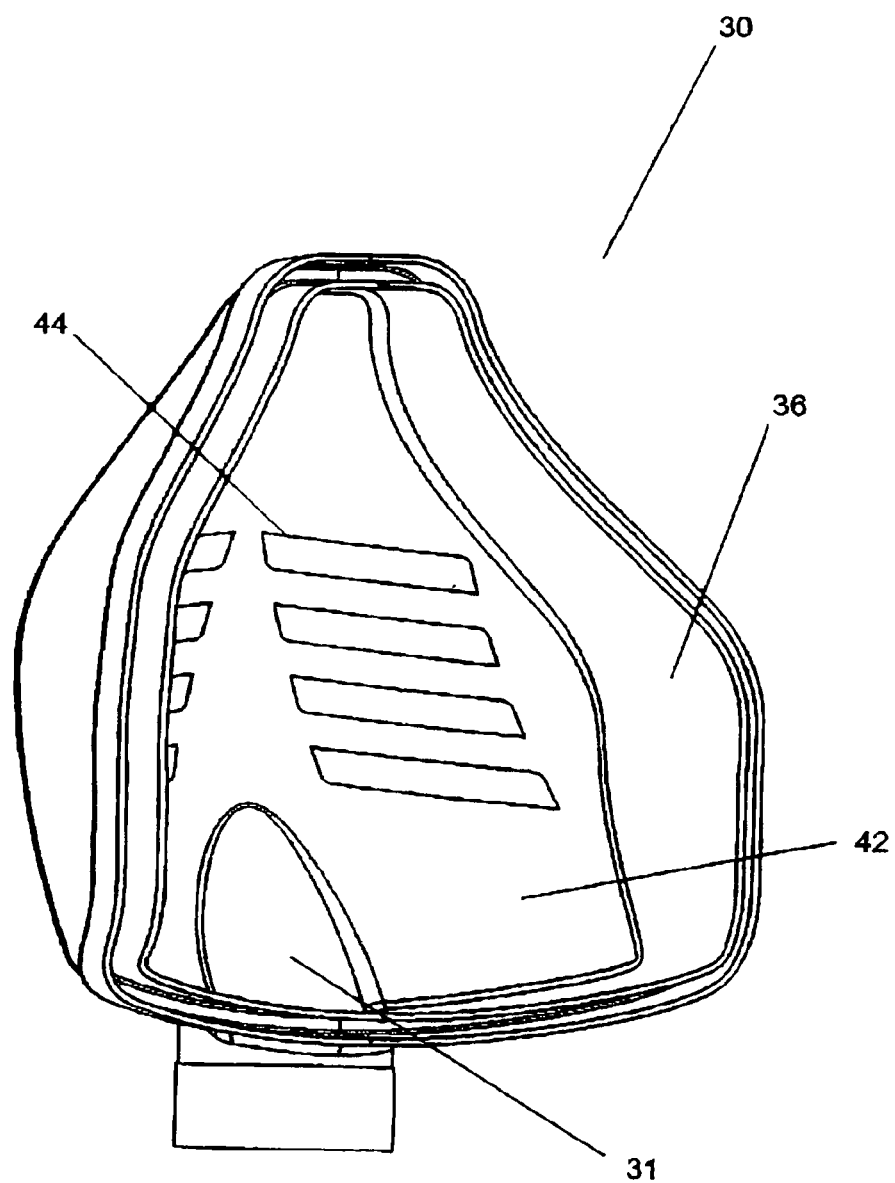
FIG. 6 is a rear view of the patient interface of FIG. 5 illustrating the bead sealing arrangement.

A second embodiment of the patient interface of the present invention is shown in FIGS. 5 and 6. The hollow body 30 is constructed of a relatively inflexible material and comprises a rigid outer circumference surface 36 and a front surface 43 to which the inspiratory conduit 3 is attached. The hollow body front surface 43 contains a plurality of slots 44 of equal dimension equidistant in the vertical direction about the mid-line of the front surface 43 and placed between the upper and lower sets of engaging clips 40a and 40b. The slots 44 are formed in a herring bone configuration with the distance between the mid-line of the front surface 43 to each row of slots increasing from the bottom surface of the upper engaging clips 40a towards the apex of the inlet 31. A moisture permeable film 42 is bonded to the hollow body 30 on the inside surface of the front surface 43 covering the slots 44 in order to alleviate the build-up of condensation within the patient interface during prolonged humidification treatment.

Figure 7:
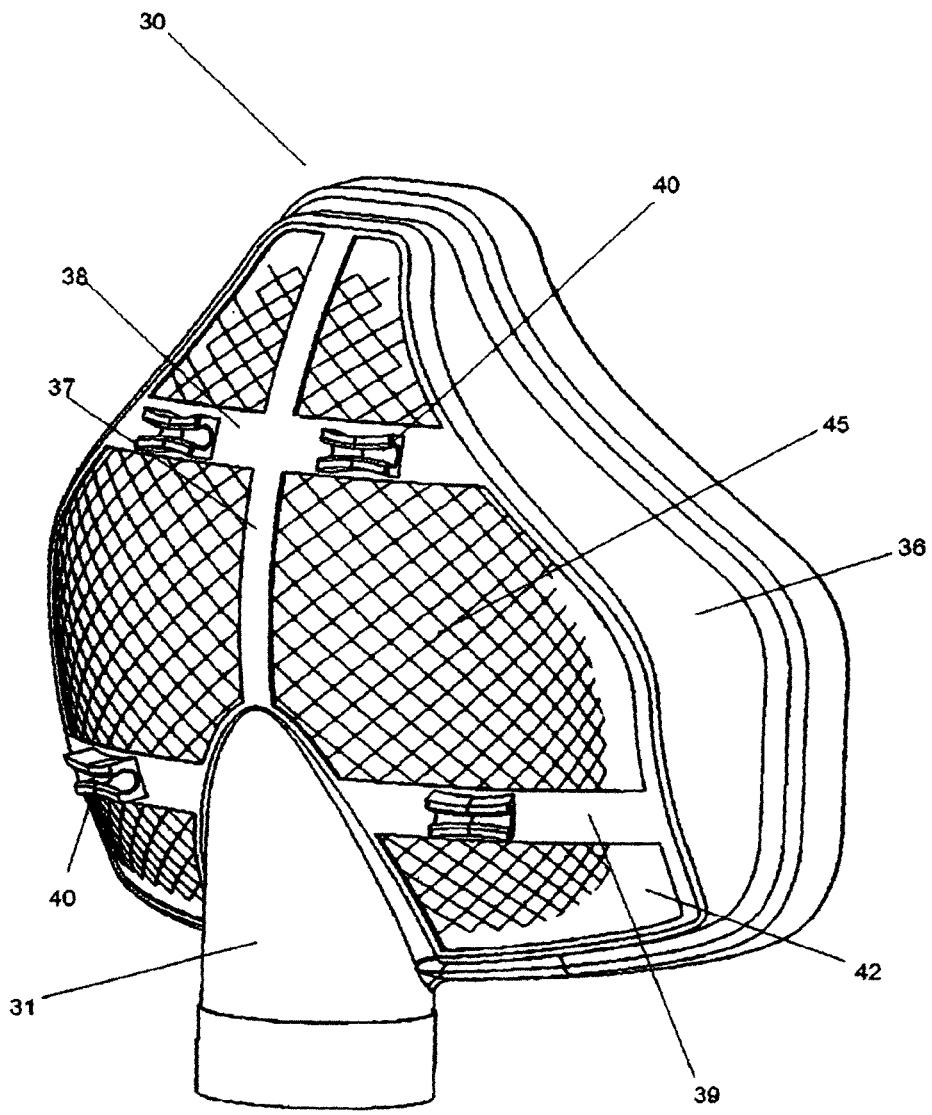
FIG. 7 is a front view of a third embodiment of a patient interface of the present invention were the interface body has a mesh surface.

A third embodiment of the patient interface of the present invention is shown in FIG. 7. The hollow body 30 is formed in the manner as described in the preferred embodiment of the present invention. A rigid mesh structure 45 is bonded to the vertical and horizontal members 37, 38 and 39 respectively and the outer circumference surface 36. A moisture permeable film 42 is further bonded to the inside surface of the hollow body framework 35 and rigid mesh 45 to alleviate the build-up of condensation within the patient interface during prolonged humidification treatment. The rigid mesh 45 provides additional strength and support to the hollow body framework 35 and a larger surface area on which to bond the moisture permeable film 42.

Figure 11:
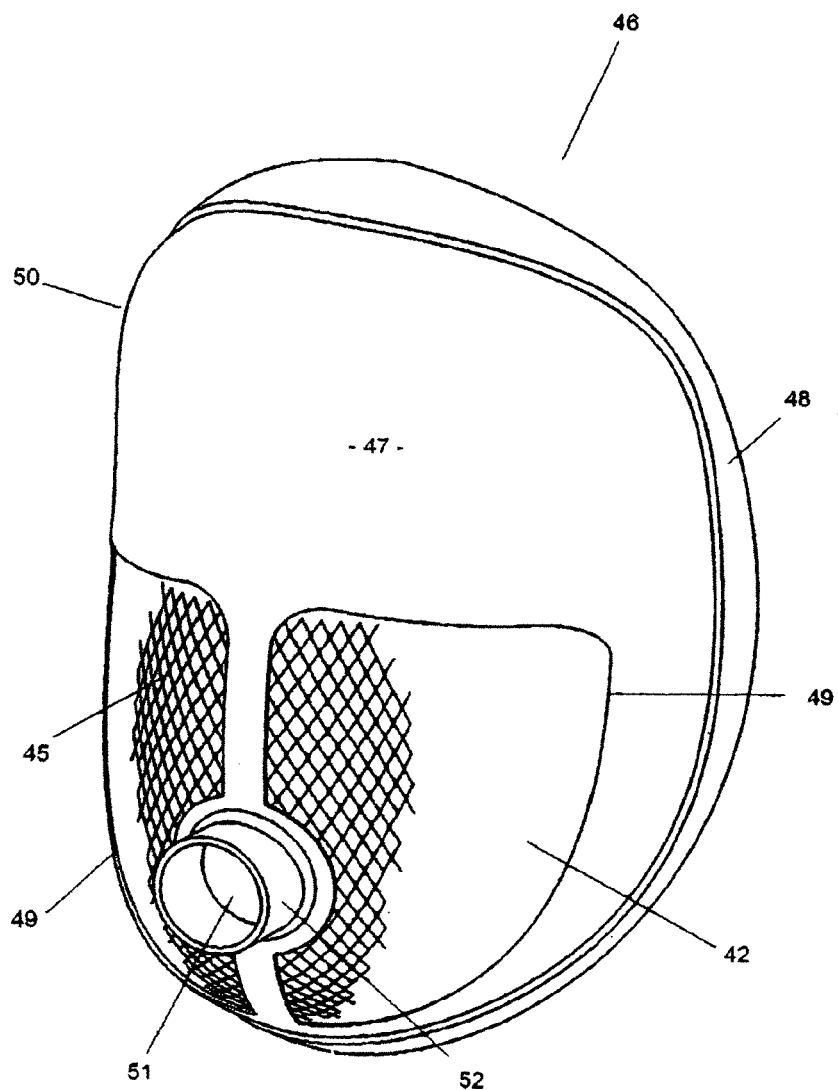
FIG. 11 is a perspective view of a fifth embodiment of the patient interface of the present invention, where the patient interface covers the full face of the user.
Figure 12:
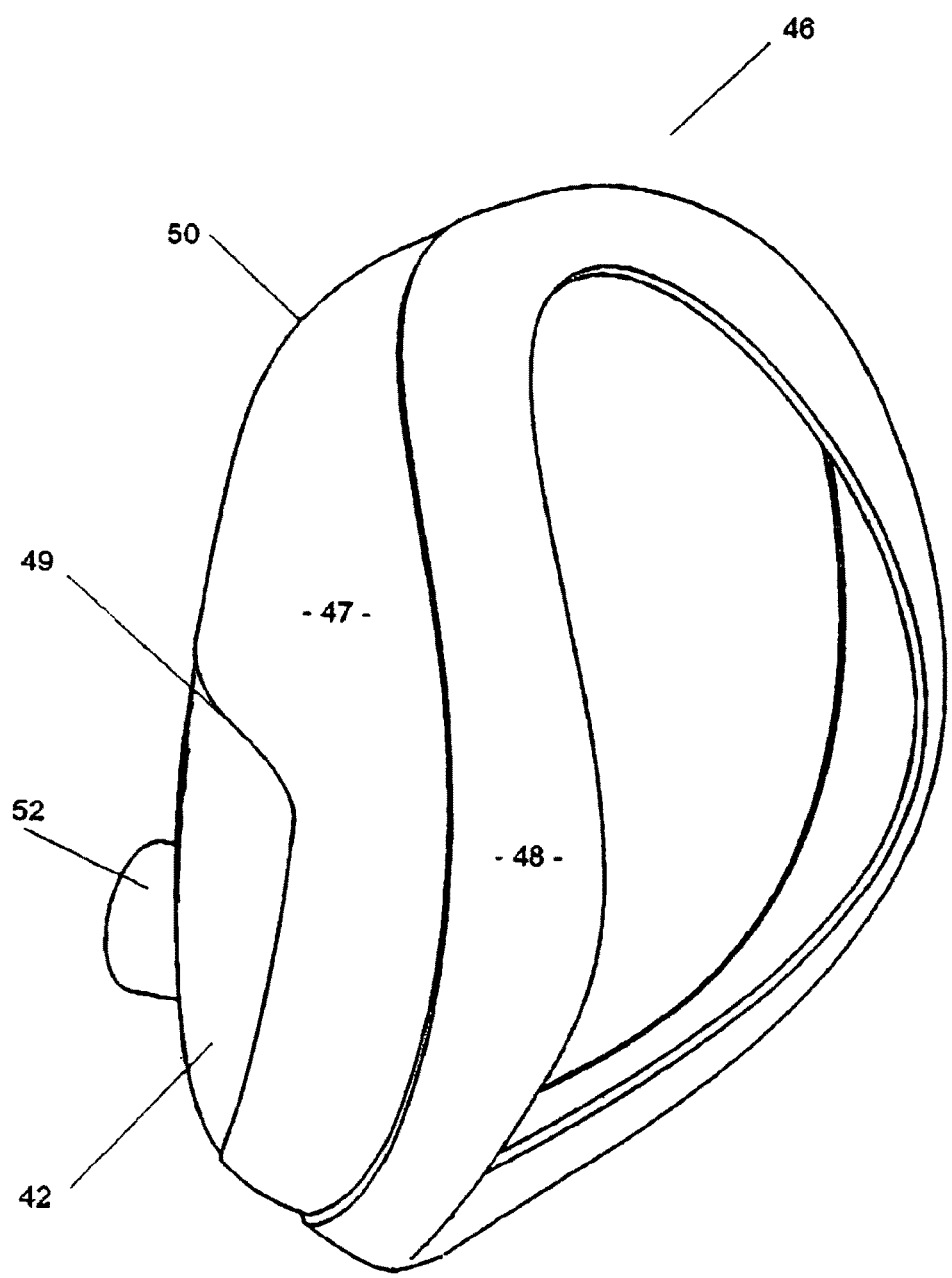
FIG. 12 is a rear perspective view of the patient interface of FIG. 12, showing the mask cushion configuration.
Figure 13:
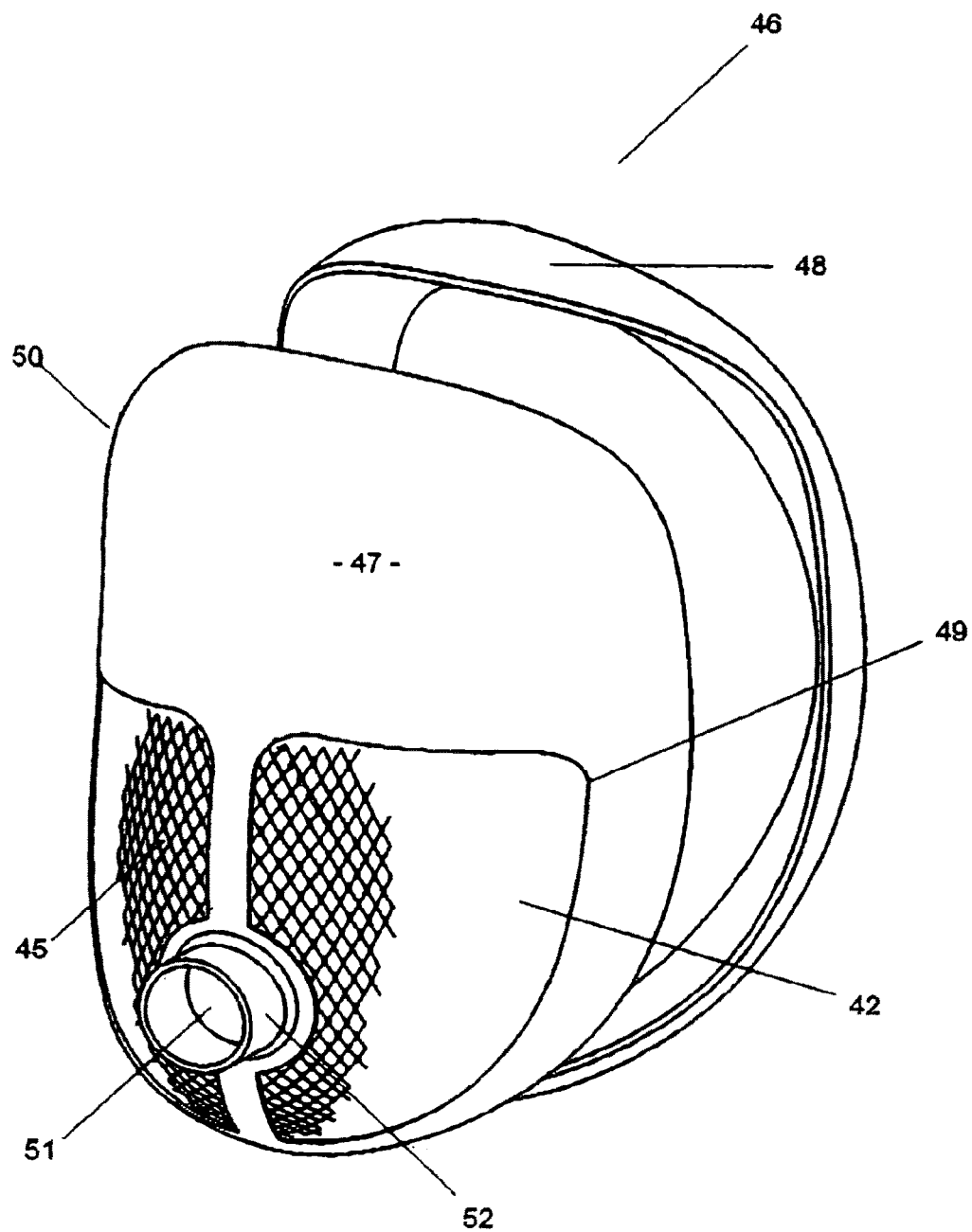
FIG. 13 is an exploded view of the patient interface of FIG. 12, showing the patient interface body and mask cushion separated.
Figure 14:
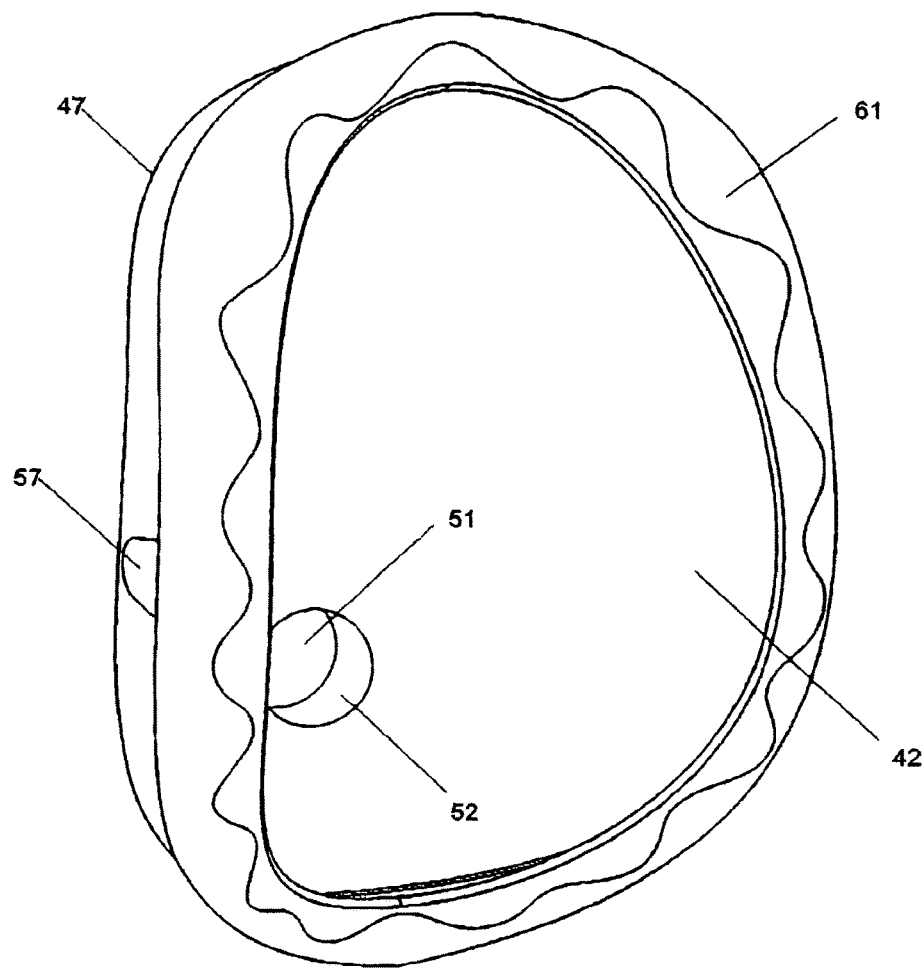
FIG. 14 is a rear view of the patient interface of FIG. 12, showing an adhesive attachment that allows the patient interface to be held on the patient's face without headgear straps.
Figure 15:
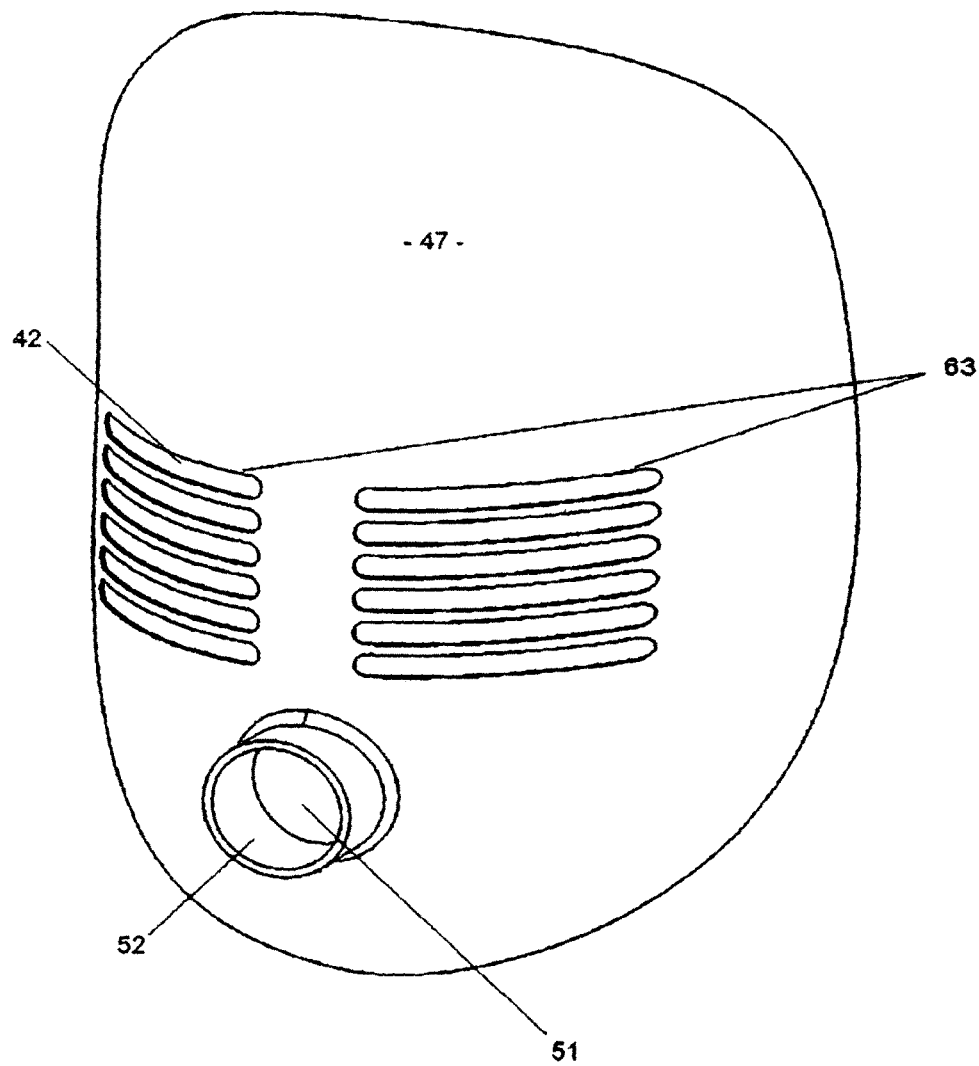
FIG. 15 is a front view of a sixth embodiment of the patient interface of the present invention were the interface body has a plurality of cut out areas in a chevron configuration.

A fourth embodiment of the patient interface may be a full face mask 46, such as shown in FIGS. 11 to 18. The patient interface 2 is capable of covering the whole face of the user 1, not merely the nose and/or mouth. The full face mask is constructed of a relatively inflexible material such as polycarbonate plastic. Such a material would provide the requisite rigidity as well as being transparent, a relatively good insulator and allows the patient to be monitored and the user to see. The patient interface 2 has a body 47 and a cushion 48, where the body includes at least one cut-out area 49 or window of moisture permeable film 42. FIG. 11 illustrates two areas of moisture permeable film 42, but any number of areas or alternatively one large window could be provided. A rigid mesh structure 45 of the type previously described may be bonded to the mask body 47 to provide additional support whilst also providing a body to which the moisture permeable film 42 can be adhered to. Alternatively, as shown in FIG. 15, the mask body 47 may have a plurality of slots 60 of the type previously described, providing a rigid surface to which the moisture permeable film 42 can be adhered to.

The mask body 47 has a tubular aperture 51 located at the front surface 50 from which a tubular extension member 52 protrudes. When in use a tube or conduit (not shown) can be attached to the tubular extension 51 to allow gases to be supplied to the interior of the patient interface 2 during treatment. The mask cushion 48 is of similar configuration to that described in relation to the nasal masks, oral masks and combination nasal-oral masks but extends around and fits the contours of the periphery of the user's face 1.

In other forms of the patient interface 2 of the present invention different configurations of the cut-out areas 34 and the placement of the moisture permeable film 42 on the mask body 30 can be varied depending on the size and application of the patient interface.

Moisture Permeable Film

The moisture permeable or breathable film 42 bonded to the interior of the patient interface 2 of the present invention is preferably a flexible and breathable membrane that allows water vapour to pass through it but not condensed water. In particular, the moisture permeable film 42 may be a hydrophilic polyester block copolymer, such as SYMPATEX®, or a perfluorosulfonate ionomer membrane, such as NAFION®.

Mask Seal

Figure 9:
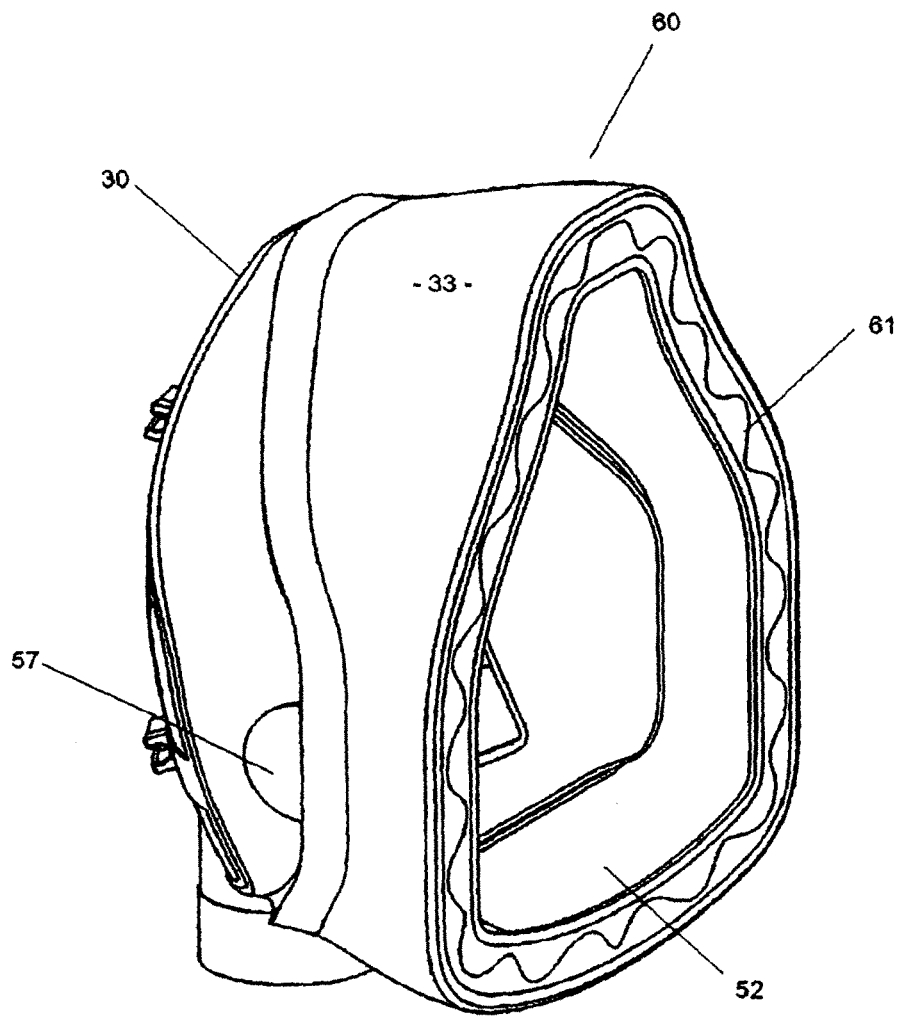
FIG. 9 is a rear view of a fourth embodiment of a patient interface illustrating an adhesive attachment that allows the patient interface to be held on the patient's face without headgear straps or other attachment means.
Figure 10:
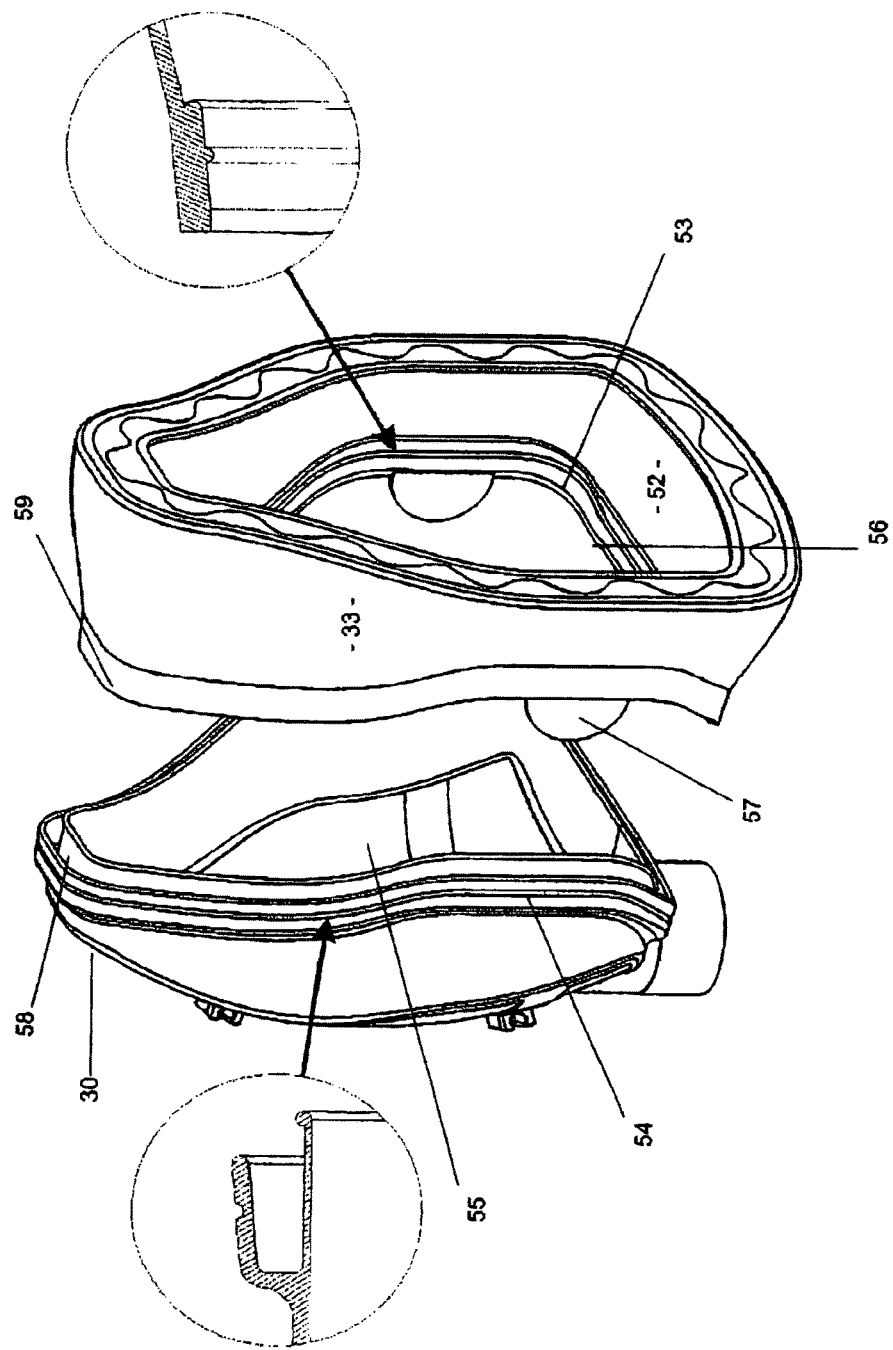
FIG. 10 is an exploded view of the patient interface of FIG. 10 showing the body to cushion locking arrangement.

Referring now to FIGS. 9 and 10, a mask cushion 33 is attached to the periphery of the hollow body 30 to provide an effective seal onto the face of the user 1 to prevent leakage. The mask cushion 33 is shaped, and is dependent on the mask type, to approximately follow the contours of a patient's face. The mask cushion 33 will deform when pressure is applied by the headgear 32 to adapt to the individual contours of any particular user.

In FIG. 10 we see that the mask cushion 33 is composed of an inner foam cushion 52 covered by an outer sealing sheath 53. The inner cushion 52 is constructed of a resilient material for example polyurethane foam, to distribute the pressure evenly along the seal around the user's face. The inner cushion 52 is located around the outer periphery 54 of the open face 55 of the hollow body 30. Similarly the outer sheath 53 may be commonly attached at its base 56 to the periphery 54 and loosely covers over the top of the inner cushion 52.

The outer sheath 53 fits in place over the cushion 52, holding it in place. The sheath 53 is secured by a snap-fit 57 to the periphery 54 of the hollow body 30. In FIG. 10 the periphery 54 is shown including an outer bead 58. The sheath 53 includes a matching bead 59, whereby once stretched around the periphery 54; the two beads 58 and 59 engage to hold the sheath 53 in place.

In the alternative embodiment shown in FIG. 9, the patient interface 1 is a strapless face mask 60 which is moulded to fit the contours of a user's face and maximise the mask-to-skin seal. An adhesive material 61 is bonded to the mask cushion 33 and is stamped in place to form substantially the same shape as the inner cushion 52 such that it fits the facial contours of the user 1. The inner cushion surface 52 is protected by a layer of cover tape (not shown) prior to use in order to maintain the adhesive properties of the adhesive material 61. When required for use the cover tape 62 is removed to reveal the adhesive material 61 on the inner cushion surface 52. The mask cushion 33 is thereby adhered to the user's face reducing the amount of leakage from the mask 60 and increasing the user's comfort by negating the requirement of the user wearing headgear. It is the intention for the mask cushion 33 of the alternative embodiment of the present invention to remain attached to the user's face for the duration of the humidification respiratory treatment. This system would allow for quick removal of the hollow body 30, enable other treatments to be administered with minimal disruption to the user 1 and increase user comfort by substantially reducing the compressive force of the patient interface 2 on the user's face.

The strapless face mask configuration as disclosed may also be applied to the full-face mask 46 as shown in FIG. 14. The adhesive material 61 is adhered to the mask cushion 48 which is shaped to fit the contours of the user's face thereby increasing user comfort and reducing the amount of gas leakage from the mask 46.

In other forms the mask cushion may be a solid cushion stamped, for example, from silicon or other similar material. Such a silicon cushion would be shaped to fit a user's facial contours and in some forms have an adhesive layer applied to allow the cushion to be adhered to the user's face for the duration of the treatment.

Headgear

To further ensure user comfort and effective pressure on the mask cushion 33, the headgear 32 may be constructed either using two straps 32a and 32b running around the back of the user's head as shown in FIG. 2 or with a partial skull cap or any other configurations as are known in the art. In this case the straps 32a and 32b or partial skull cap would be constructed using neoprene but may also be constructed using any material as is known in the art which will be comfortable for the user.

Hollow Body to Headgear Attachment

Referring now to FIG. 3 the present invention is illustrated using an upper and lower sliding strap 41 to attach the headgear 32 to the hollow body 30. The strap 41, shown in FIG. 8 in isolation, is constructed of polyacetal (Dehin 500P NC010) using injection moulding techniques to give a polished finish. This material is similar to other nylon based derivatives, with its polished finish having a particularly low friction co-efficient, and therefore slides with respect to the hollow body 30 with very little resistance.

As shown in FIG. 3, the hollow body 30 includes a number of engaging clips 40 connected to the upper and lower horizontal members 38 and 39 respectively ensuring adequate direct force on the mask cushion 33 to the user's face thereby minimizing mask-to-skin leaks. In use the sliding strap 41 snaps into place into engaging clips 40 and can only be removed therefrom using a substantial force. This means that with any normal use the sliding strap 41 will stay retained within the engaging clips 40.

Figure 8:
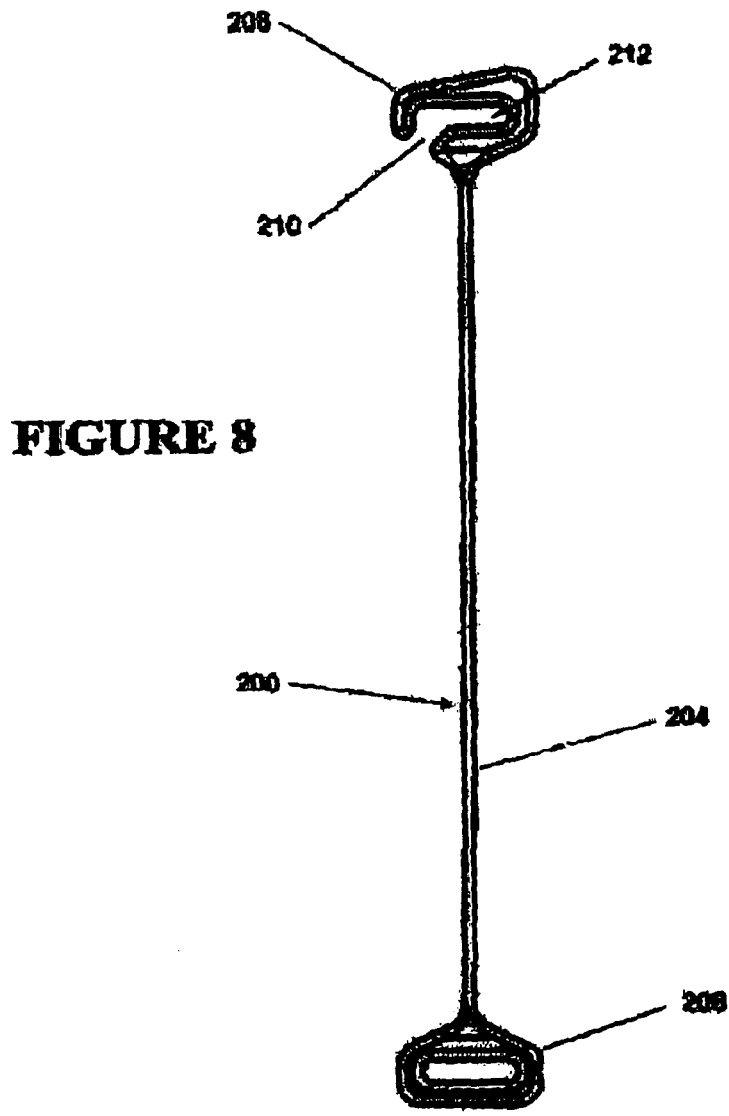
FIG. 8 is a side view of the sliding strap.

FIG. 8 illustrates the sliding strap which is described in our co-pending New Zealand application number 514184 and is herein described by way of reference. The sliding strap includes a mid-section 204 intended to reciprocate with the engaging clips 40, terminated at each end by loops 206, 208 which attach to the headgear 32. The first loop 206 is a full loop through which the headgear 32 may be permanently attached with for example, a Velcro™ strap. The loop 208 at the other end, is a partial loop 210 designed so that a strap or loop from the headgear 32 can be easily slipped in or out of the open section 212 to allow easy removal and attachment of the mask.

The present invention as shown in FIG. 3 uses two sliding straps 41 which are terminated at each end by loops 208 being partial loops 210. This sliding strap configuration is used to allow easy connection to the headgear straps 32 plus removal and attachment of the mask.

Figure 16:
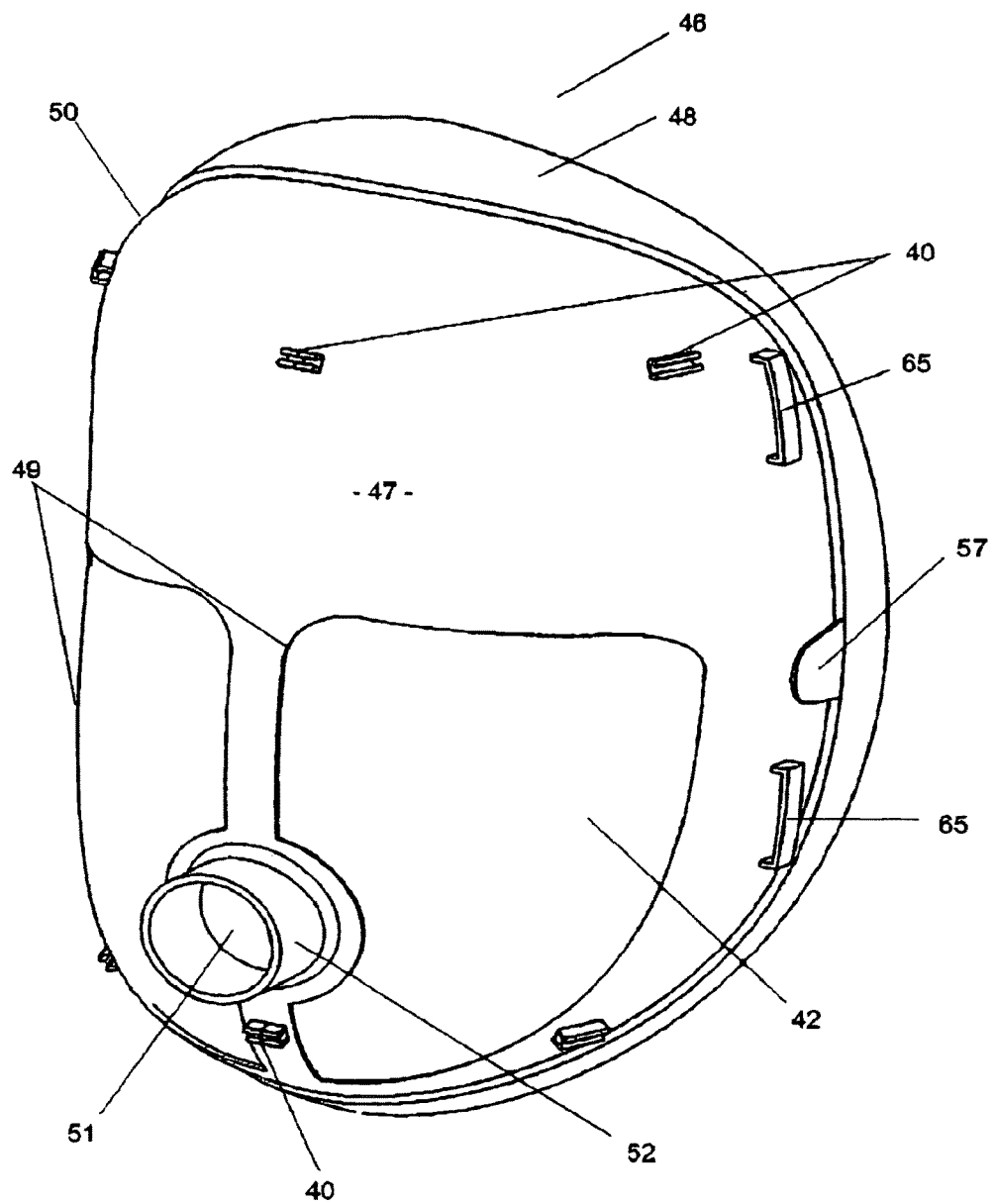
FIG. 16 is a front view of the patient interface of FIG. 12, showing the upper and lower engaging clips and headgear strap attachment points.

Referring now to the fourth embodiment of the present invention. FIG. 16 shows a full-face mask 46 having an upper and lower set of engaging clips 40 attached to the mask front surface 47. In use the sliding straps 41 as previously described in the present invention, snap into place into the engaging clips 40. The mask front surface 47 also shows an upper and lower set of headgear attachment points 65 permanently fixed to the upper portion and lower portion of the periphery of the front surface 47 which in use Velcro™ straps, connected to the end portion of the headgear straps 66, may be attached.

Full Face Mask Headgear

Figure 17:
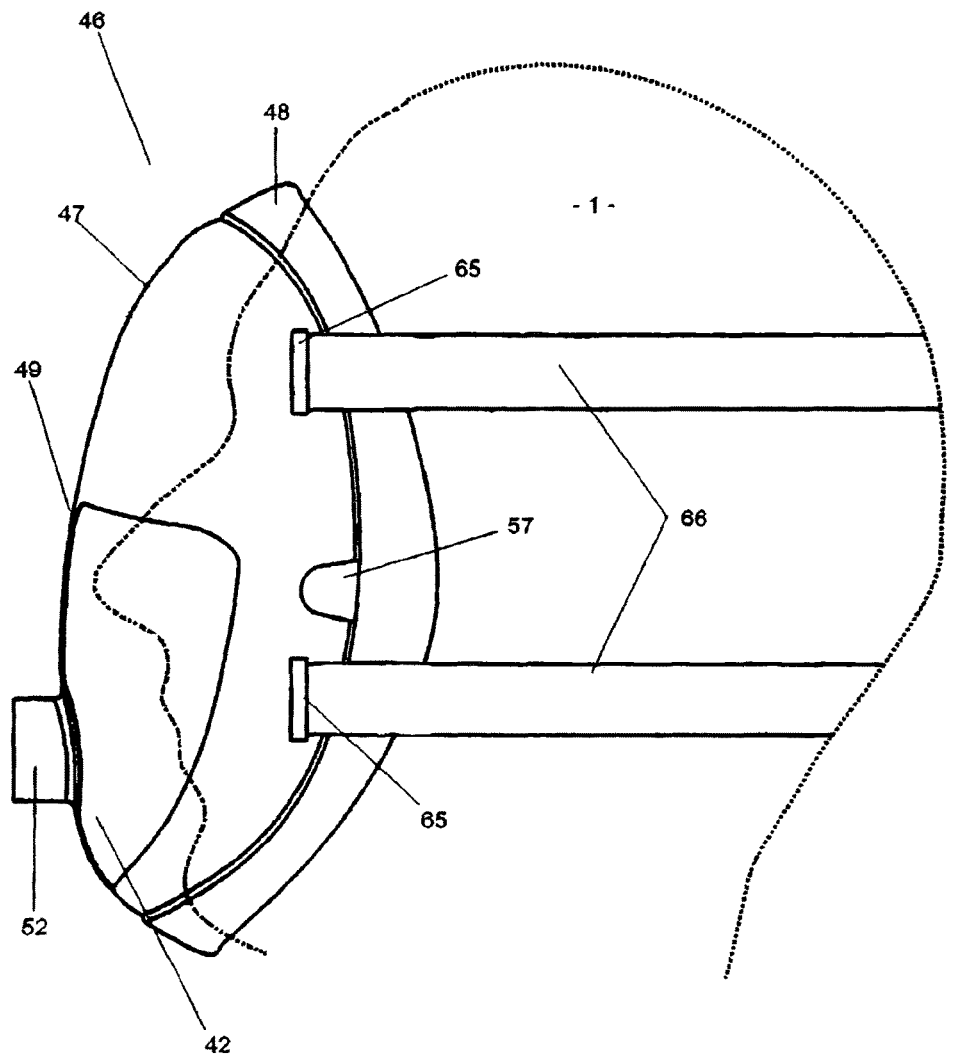
FIG. 17 is a front perspective view of the patient interface of FIG. 12, showing mask attachment to the user's face using headgear straps.

In a further form of the present invention the headgear assembly comprises an upper and a lower adjustable strap member 66 which runs around the back of the user's head 1 as shown in FIG. 17. In this case the straps 66 would be constructed using neoprene but may also be constructed using any material as is known in the art which will be comfortable for the user 1. As illustrated in FIG. 17, two sets of headgear attachment points 65 are permanently fixed to the periphery of the upper portion and lower portion of the full-face mask 46 to which the upper and lower adjustable straps 66 are attached. Headgear adjustment means is achieved using Velcro™ near the end portions of the upper and lower straps 66 to ensure user comfort and effective pressure on the mask cushion 48 to minimize gas leakage from the mask 46.

Figure 18:
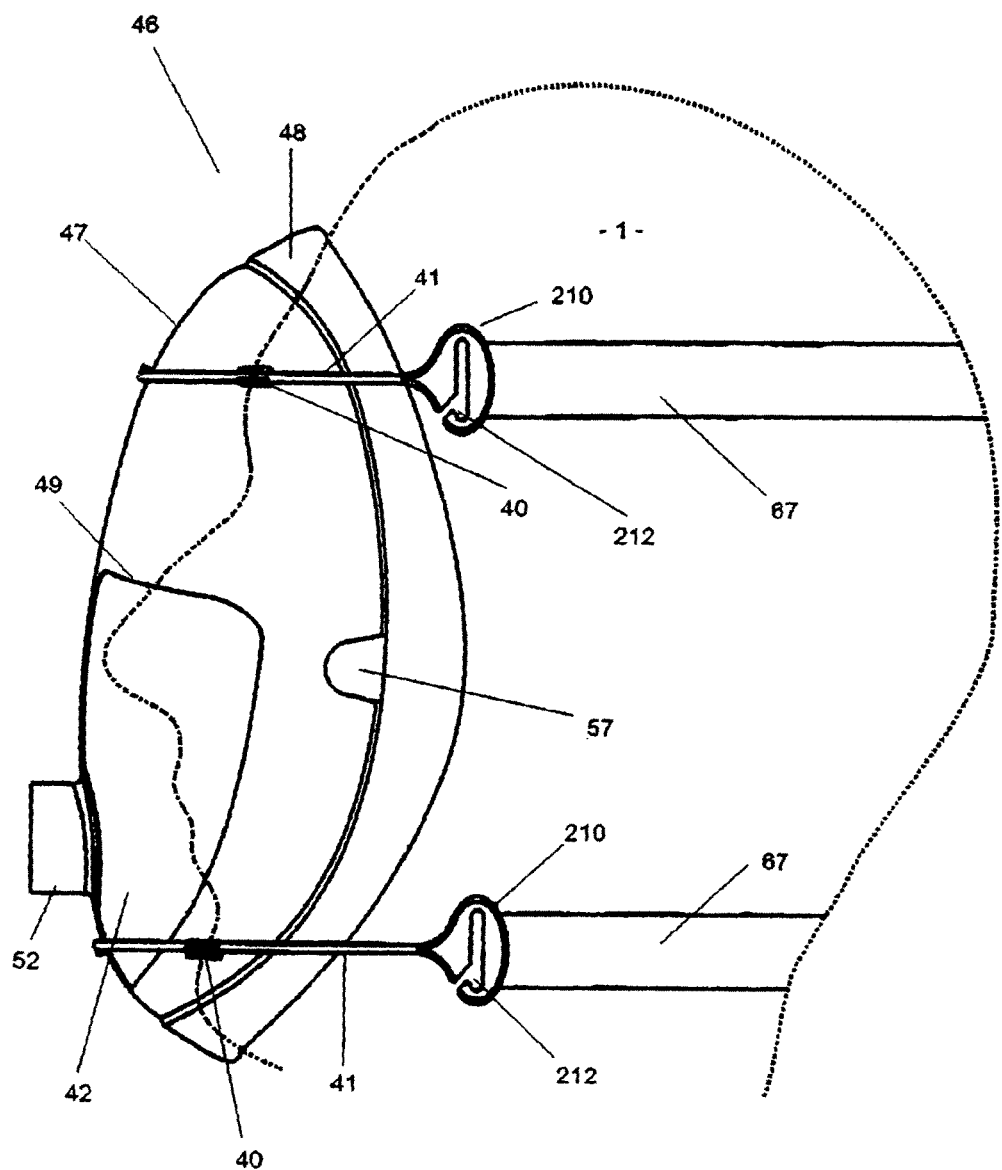
FIG. 18 is a front perspective view of the patient interface of FIG. 12, showing mask attachment to the user's face using sliding straps attached to headgear straps.

Referring now to FIG. 18 an alternative form of the present invention is shown using an upper and lower sliding strap 41 to attach the headgear 67 to the full-face mask front surface 47. In use, the sliding straps 41 snap into the upper and lower engaging clips 40. The sliding straps are terminated at each end by partial loops 210 so that a strap or loop from the upper and lower headgear members 67 can be easily slipped in or out of the open section 212 to allow easy removal and attachment of the full-face mask 46. Headgear adjustment means is achieved using Velcro™ near the end portions of the upper and lower straps 67 to ensure user comfort and effective pressure on the mask cushion 48 to minimize gas leakage from the mask 46.

What is claimed is:

1. A patient interface comprising:
   a rigid body having a front surface comprising a framework and a plurality of cut out areas, a surface area of the plurality of cut out areas being greater than a surface area of the framework;
   a mask cushion attached to the rigid body and configured to contact the user's face and provide a seal against the user's face;
   an inlet positioned on the rigid body, the inlet defining a coupling for fluid connection to a gas delivery system;
   a water vapor breathable layer that is provided to the body to allow water vapor to pass through but not condensed water, whereby the water vapor breathable layer alleviates the build up of condensation within the body, wherein the water vapor breathable layer comprises a hydrophilic, moisture permeable material.

2. The patient interface as claimed in claim 1 the water vapor breathable layer is attached to rigid body, the rigid body defining a hollow body to define a breathing chamber.

3. The patient interface as claimed in claim 1 wherein each cut out area is covered by the water vapor breathable layer.

4. The patient interface as claimed in claim 1 wherein each cut out area is a slot cut-out in the rigid body.

5. The patient interface as claimed in claim 1 wherein the plurality of cut out areas comprises a plurality of slots of equal dimension equidistant in the vertical direction about a mid-line of the front surface of the rigid body.

6. The patient interface as claimed in claim 1 wherein the framework comprises an outer circumferential surface, a vertical member extending from an apex of the outer circumferential surface to an apex of the inlet, an upper horizontal cross member and a lower horizontal cross member.

7. The patient interface as claimed in claim 1 wherein the rigid body includes an inner surface and a rigid mesh, the rigid mesh attached to the inner surface.

8. The patient interface as claimed in claim 6 wherein the rigid body includes an inner surface and a rigid mesh, and wherein the rigid mesh is bonded to the vertical member, the upper horizontal cross member, and the lower horizontal cross member and to the outer circumferential surface and the water vapor breathable layer is bonded to an underside of the rigid mesh.

9. The patient interface of claim 1 wherein the plurality of cut out areas are formed in a herring bone configuration.

10. The patient interface as claimed in claim 1 wherein the water vapor breathable layer is disposed on an inner side of the rigid body such that the water vapor breathable layer overlies at least one of the plurality of cut out areas in the rigid body.

11. The patient interface as claimed in claim 1 wherein the water vapor breathable layer is a moisture permeable film.

12. The patient interface as claimed in claim 7 wherein the water vapor breathable layer is attached to an inner surface of the rigid mesh.

13. The patient interface as claimed in claim 1 wherein the water vapor breathable layer is water vapor permeable but air impermeable, allowing water vapor to pass through while not allowing the transmission of air.

14. The patient interface as claimed in 11 wherein the moisture permeable film is configured to allow the passage of water vapor out of the rigid body, while not allowing the passage of air from the rigid body.

15. The patient interface as per claim 11 wherein the moisture permeable film is bonded to an underside of the mesh structure.

16. The patient interface as claimed in claim 1 further comprising a headgear adapted to hold the patient interface in position on a head of the user.

17. The patient interface as claimed in claim 16 wherein the interface comprises a slide member mounted to the rigid body in use and adapted to connect the headgear to the patient interface when a user is using the patient interface.

18. The patient interface as claimed in claim 1 wherein the water vapor breathable layer is a moisture permeable film formed of a hydrophilic polyester block copolymer or perfluorosulfonate ionomer membrane.

19. The patient interface as claimed in claim 1 wherein at least one of the plurality of cut out areas is disposed below a transverse centerline of the rigid body, and wherein at least one of the plurality of cut out areas is disposed above the transverse centerline of the rigid body.

* * * * *

UNITED STATES PATENT AND TRADEMARK OFFICE
CERTIFICATE OF CORRECTION

PATENT NO. : 10,357,625 B2
APPLICATION NO. : 14/661314
DATED : July 23, 2019
INVENTOR(S) : Brett John Huddart et al.

Page 1 of 1

It is certified that error appears in the above-identified patent and that said Letters Patent is hereby corrected as shown below:

On the Title Page

On Page 3, Column 2, Item (56), Line 51, under Other Publications, change "membrate" to --membrane--.

On Page 3, Column 2, Item (56), Line 54, under Other Publications, change "Regsitered" to --Registered--.

On Page 3, Column 2, Item (56), Line 63, under Other Publications, change "Cirucuits;" to --Circuits;--.

In the Claims

In Column 8, Line 31, in Claim 2, after "claim 1" insert --wherein--.

In Column 9, Line 8, in Claim 14, after "in" insert --claim--.

Signed and Sealed this
Twenty-ninth Day of October, 2019

Andrei Iancu
*Director of the United States Patent and Trademark Office*